Figure 1:
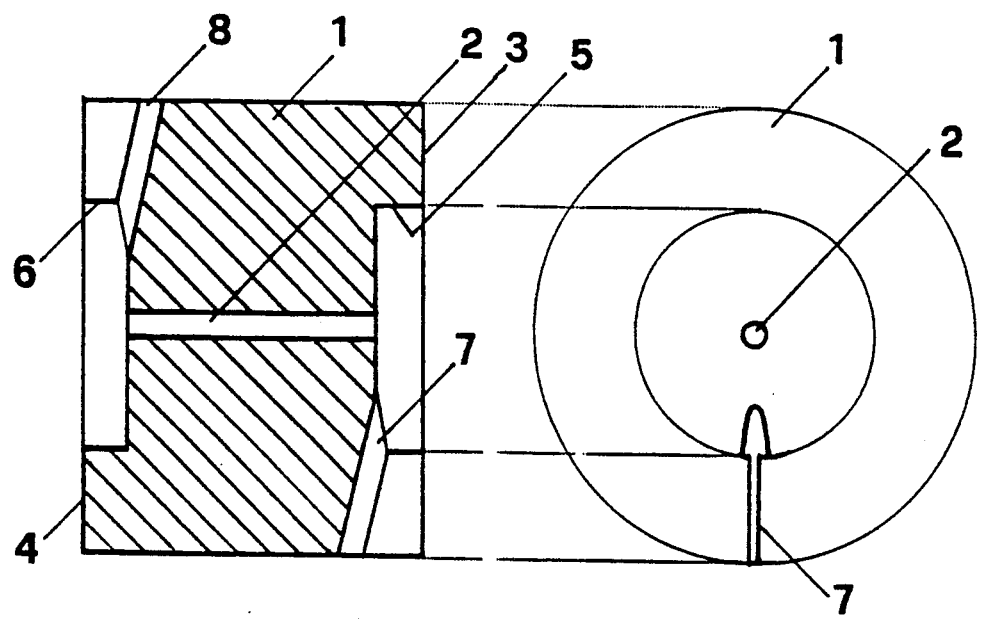

United States Patent [19]
Chervet

[11] Patent Number: 5,057,216
[45] Date of Patent: Oct. 15, 1991

[54] CAPILLARY FLOW CELL

[75] Inventor: Jean-Pierre Chervet, Amsterdam, Netherlands

[73] Assignee: Kontron Instruments Holding NV, Curacao, Netherlands Antilles

[21] Appl. No.: 499,699

[22] Filed: Mar. 27, 1990

[30] Foreign Application Priority Data

Apr. 14, 1989 [EP] European Pat. Off. ............ 89106700

[51] Int. Cl.$^5$ .............................................. B01D 15/08
[52] U.S. Cl. .................................... 210/198.2; 55/386; 422/70; 73/61.1 C
[58] Field of Search ....................... 210/198.2; 55/386; 422/70; 73/61.1 C

[56] References Cited

U.S. PATENT DOCUMENTS

| | | |
|---|---|---|
| 4,375,163 | 3/1983 | Yang ................................. 73/61.1 C |
| 4,575,424 | 3/1986 | Allington et al. ................ 210/198.2 |
| 4,854,700 | 8/1989 | Cutie et al. ...................... 73/61.1 C |

FOREIGN PATENT DOCUMENTS 0266769 11/1987 European Pat. Off. .
2621895 12/1977 Fed. Rep. of Germany .

Primary Examiner—Stanley S. Silverman
Assistant Examiner—Neil M. McCarthy
Attorney, Agent, or Firm—Morgan & Finnegan

[57] ABSTRACT

A capillary flow cell in which a capillary (9) partially extends along the optical path of the cell and has its two end portions (12,13) bent to achieve an essentially Z-shaped configuration. A template (1) has a central bore (2) in which the middle part (11) of the capillary (9) is positioned. A method of manufacture of this capillary flow cell comprises the steps of a) inserting a capillary in a central bore of a template,
b) heating the capillary immediately outside the bore to soften the capillary material
c) bending the two ends to achieve an essentially Z-shaped or U-shaped configuration.

1 Claim, 1 Drawing Sheet

CAPILLARY FLOW CELL

This invention relates to a capillary flow cell for use in microseparation techniques such as capillary liquid chromatography (LC), supercritical fluid chromatography (SFC), capillary zone electrophoresis (CZE) and related techniques and to a method of manufacture of the cell.

During the last years miniaturization has become an important task in analytical chemistry. The introduction of micro HPLC and other separation techniques such as the capillary zone electrophoresis (CZE) emphasize this tendency. However, sensitive detection with virtually no dead volume is still difficult, especially in the field of light absorbance detection such as UV/VIS. The need for detectors with small cell volumes has been successfully solved in many instances. UV detectors with cell volumes of only 5-100 nl have been reported and several detectors with a volume of only a few nanoliters are commercially available.

So far, most of these detector cells are based on a simple capillary which is introduced perpendicularly to the light beam of the detector (on-column detection approach).

Such configurations show extremely small volumetric dispersions but due to the short optical path length of the flow cell, given by the inner diameter of the capillary, they suffer enormously from poor sensitivity in UV/VIS detection. It is, therefore, the object of this invention to provide a capillary microflow cell with a configuration which offers the advantages of both low dead volumes and significantly enhanced sensitivity.

This is achieved by a capillary flow cell in which a capillary partially extends along the optical path of the cell and has its two end portions bent to achieve an essentially Z-shaped configuration, and a template with a central bore in which the middle part of the capillary is positioned.

In the following an embodiment thereof is described with reference to the accompanying drawing. It is shown in FIG. 1 an example of a flow cell holder (template), FIG. 2 the same template as in FIG. 1 with the capillary inserted.

The flow cell holder or template 1 shown in FIG. 1 in cross-section and in side view is an essentially cylindrical disc with a central through bore 2. Both flat end faces 3, 4 of the disc are provided with circular recesses 5, 6 of about half the diameter of the disc. Narrow radial grooves 7, 8 connect on each side the respective recess with the cylindrical outer surface of the disc. The narrow grooves are offset by 180° to each other.

The disc is made of stainless steel. Other materials would be useful as well. Preferably the material should be made of heat resistant, chemically inert material.

The thickness of the disc, i.e. the distance between the two end faces depends on the desired optical path length of the cell. In the present case the thickness is about 23 mm. The central bore has a diameter of about 1.6 mm and the circular recesses have a width of about 16 mm. The grooves have a width of about 0.5 mm. Of course, these dimensions may vary depending on the specific design and parameters of the flow cell.

Figure 2:
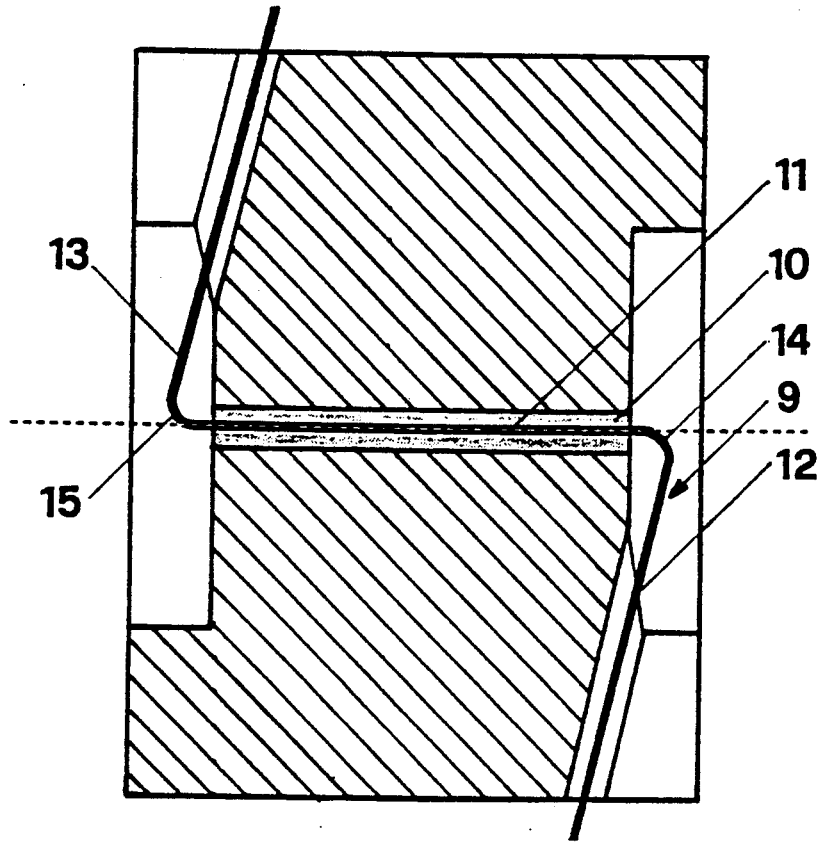

The manner in which the capillary 9 is arranged in the template is shown in FIG. 2. For optimum centering of the capillary in the bore a short piece of tubing 10 is used as an insert. The insert consists of either stainless steal as the template itself or of glass line tubing, reflecting glass tubing etc. Advantageously the insert has an inner diameter which is close to the outer diameter of the capillary. The insert is fixed in the template central pore with epoxy glue.

A capillary 9 is arranged with its middle portion 11 in the bore of the insert. The two ends 12, 13 of the capillary are bent immediately outside of the insert by about 100° in opposite directions to an another such that they extend through the grooves towards the cylindrical outside of the template.

The capillary consists of fused silica coated with polyimide. The middle portion of the capillary is not coated.

The middle portion of the capillary defines the optical path of the flow cell. The two bends 14, 15 constitute the entrance and exit window for the light beam.

As mentioned above, the total path length of the flow cell is dependent on the length of the chosen template and of the instrumental set-up of the detection device. Starting from conventional UV/VIS detectors templates with length of 2 to 25 mm can easily be constructed. The construction of longer templates of varying lengths is possible using this technique and results in very long flow cell configurations for UV/VIS detection.

The evaluation of the tubing for the construction of the flow cell depends upon the desired volume, detection mode and separation technique. For capillary HPLC with flow rates of ca. 1-10 μl/min the selected tubing should not exceed an inner diameter of 75 μm, otherwise the dispersion in the detector affects the efficiency of the separation. For capillary SFC or CZE smaller I.D., e.g. $\leq$ 25 μm are required.

The manufacture of the flow cell is as follows.

Before introducing the capillary into the insert, the polyimide must be removed from the capillary for a length corresponding to the thickness of the template (i.e. 23 mm) by burning off the coating with a gas burner or a hot flame. The clean quartz glass, i.e. uncoated fused silica capillary, possess enough light transparency to make UV/VIS or fluorescence detection, etc., possible. The use of lenses or fiber optics for focussing the light beam through the flow cell is highly recommended to reduce the amount of light scattering. For bending the capillary into its final position (e.g., longitudinal configuration) the tubing is heated again till its softens and thereby, can be bent. Due to the bending no quartz glass windows are required any more and the entire flow cell is made only by the capillary tube itself.

Besides the advantages mentioned above, the flow cell resists very high pressures up till 10,000 psi (ca. 700 bar). The pressure stability is dependent on the thickness of the wall of the capillary tubing (e.g. inner diameter 75 μm, outer diameter 260 μm, wall thickness ca. 92 μm, pressure stability $\geq$ 8700 psi/600 bar). Consequently, longitudinal capillary flow cells as described in this invention are ideal for UV detection in SFC.

With this new configuration sensitivity enhancement is significant, at least 100 times that of previous detection devices. This is in accord with Lambert-Beer law, which states that the sensitivity is directly proportional to the path length of the flow cell. In addition, this new flow cell construction has virtually no dead volume. By using capillary tubing of inner diameters of smaller than 50 μm, flow cells with total volumes of a few nanoliters can be constructed.

I claim:

1. Capillary flow cell comprising an optical path, a capillary (9) which partially extends along the optical path of the cell, the capillary having two end portions (12, 13) bent to achieve an essentially z-shaped configuration, and a template (1) with a central bore (2) in which a middle part (11) of the capillary is positioned.

* * * * *